(12) United States Patent
Larsen et al.

(10) Patent No.: US 12,415,184 B2
(45) Date of Patent: Sep. 16, 2025

(54) DEVICE FOR ANALYSIS OF CELLULAR MOTILITY

(71) Applicant: MOTILITYCOUNT APS, Copenhagen NV (DK)

(72) Inventors: Jacob Mollenbach Larsen, Copenhagen NV (DK); Steen Broch Laursen, Odense (DK)

(73) Assignee: MOTILITYCOUNT APS, Copenhagen NV (DK)

( * ) Notice: Subject to any disclaimer, the term of this patent is extended or adjusted under 35 U.S.C. 154(b) by 1014 days.

(21) Appl. No.: 17/497,798

(22) Filed: Oct. 8, 2021

(65) Prior Publication Data

US 2022/0023864 A1 Jan. 27, 2022

Related U.S. Application Data

(60) Division of application No. 16/929,791, filed on Jul. 15, 2020, now Pat. No. 11,701,655, which is a continuation of application No. 14/888,700, filed as application No. PCT/DK2014/050117 on May 2, 2014, now abandoned.

(30) Foreign Application Priority Data

May 3, 2013 (DK) .................................. 201370251

(51) Int. Cl.
| | | |
|---|---|---|
| *B01L 3/00* | (2006.01) | |
| *G01N 1/40* | (2006.01) | |
| *C12M 1/34* | (2006.01) | |
| *G01N 15/00* | (2006.01) | |
| *G01N 15/01* | (2024.01) | |

(52) U.S. Cl.
CPC ...... *B01L 3/502753* (2013.01); *G01N 1/4077* (2013.01); *B01L 2300/04* (2013.01); *B01L 2300/0681* (2013.01); *B01L 2300/087* (2013.01); *B01L 2400/0478* (2013.01); *B01L 2400/0487* (2013.01); *C12M 41/46* (2013.01); *G01N 2001/4088* (2013.01); *G01N 2015/0003* (2013.01); *G01N 15/01* (2024.01)

(58) Field of Classification Search
CPC ........... G01N 15/01; G01N 2015/0003; G01N 1/4005; G01N 33/689; B01L 3/502753
See application file for complete search history.

(56) References Cited

U.S. PATENT DOCUMENTS

| 5,296,375 A | 3/1994 | Kricka et al. |
| 5,459,068 A | 10/1995 | Madara |
| 6,129,214 A | 10/2000 | Bar-Ami et al. |
| 2005/0158700 A1 | 7/2005 | Brickwood |

FOREIGN PATENT DOCUMENTS

| CA | 1329786 C | 5/1994 |
| RU | 2475539 C2 | 10/2010 |
| WO | 96/14933 | 5/1996 |
| WO | 0009648 A1 | 2/2000 |
| WO | 01/60968 A1 | 8/2001 |
| WO | 2004/026154 A1 | 4/2004 |
| WO | 2005/027634 A1 | 3/2005 |
| WO | 2007/129292 A1 | 11/2007 |
| WO | 2008028081 A2 | 3/2008 |
| WO | 2008/121437 A2 | 10/2008 |
| WO | 2012126478 A1 | 9/2012 |
| WO | 2012162181 A2 | 11/2012 |
| WO | 2015077333 A1 | 5/2015 |

OTHER PUBLICATIONS

Henkel et al. "Sperm preparation for ART" Reproductive Biology and Endocrinology, 2003 1:108 22 pages (Year: 2003).*
Danish Search Report for Danish priority Application No. PA201370251, completed Dec. 17, 2013, (4 pp.).
PCT International Search Report for PCT International Patent Application No. PCT/DK2014/050117, mailed Jul. 21, 2014 (6 pp.).
Nasr-Esfahani, M.H., et al., "Sperm MTT Viability Assay: A New Method for Evaluation of Human Sperm Viability," Journal of Assisted Reproduction and Genetics, vol. 19, No. 10, Oct. 2002, pp. 477-482.
Davies, Ryan T., et al., Microfluidic Filtration System to Isolate Extracellular Vesicles from Blood, Lab on a Chip, The Royal Society of Chemistry (2012), vol. 12, No. 24, 5202-5210.
Kobayashi, Taizo et al., Microfluidic Chip with Serially Connected Filters for Improvement of Collection Efficiency in Blood Plasma Separation, Sensors and Actuators B 161 (2012) 1176-1183.
Strzemienski, P.J., et al., Evaluation of Cellulose Acetate/Nitrate Filters for the Study of Stallion Sperm Motility, J. Reprod. Fert., Suppl. 35 (1987), 33-38.
Tasoglu, Savas, et al. Manipulating Biological Agents and Cells in Micro-Scale Volumes for Applications in Medicine, Chem. Soc. Rev. (2013) 42, 5788-5808.
Tomlinson, Mathew et al., Sperm Quality and its Relationship to Natural and Assisted Conception: British Fertility Society Guidelines for Practice, Human Fertility (2013), Early Online: 1-19, The British Fertility Society.

(Continued)

*Primary Examiner* — Thane Underdahl
(74) *Attorney, Agent, or Firm* — McCormick, Paulding & Huber PLLC

(57) ABSTRACT

A mesoscale fluidic system comprises a substrate having a sample chamber and an analysis chamber. The sample chamber comprises a cell permeable filter defining a sample application compartment and a conditioning medium compartment. The sample chamber has a sample inlet port in the sample application compartment. The analysis chamber has an entry port and an exit port. The conditioning medium compartment is in fluid communication with the entry port of the analysis chamber via a channel. The sample application compartment is below the cell permeable filter and the conditioning medium compartment is above the cell permeable filter. The mesoscale fluidic system is suited for analysing cellular motility in a sample. Also disclosed is a method of estimating the quantity of motile cells in a sample and a method of extracting motile cells from non-motile cells.

2 Claims, 3 Drawing Sheets

(56) References Cited

OTHER PUBLICATIONS

Wei, Huibin et al., Particle Sorting Using a Porous Membrane in a Microfluidic Device, Supp. Material (ESI) for Lab on a Chip, The Royal Society of Chemistry (2010), 5 pages.
Wei, Huibin et al., Particle Sorting Using a Porous Membrane in a Microfluidic Device, Lab Chip, The Royal Society of Chemistry (2011), 11, 238-245.
World Health Organization, WHO Laboratory Manual for the Examination and Processing of Human Semen, 5th Ed. (2010).
Zheng, Siyang et al., 3D Microfilter Device for Viable Circulating Tumor Cell (CTC) Enrichment from Blood, Biomed. Microdevices (2011), 13, 203-213.
Bras, et al. "Transcellular translocation of Campylobacter jejuni across human polarised epithelial monolayers" FEMS Microbiology Letters 179 (1999) 209-215 (Year: 1999).
Owen, et al. "A Review of the Physical and Chemical Properties of Human Semen and the Formulation of a Semen Simulant" Journal of Andrology, vol. 26, No. 4, Jul./Aug. 2005 (Year: 2005).
Hulkower, et al. "Cell Migration and Invasion Assays as Tools of Drug Discovery" Pharmaceutics 2011, 3, 107-124.
Ludwig, et al., "The electrical resistance breakdown assay determines the role of proteinases in tumor cell invasion" Am J Physiol Renal Physiol 283: F319-327, 2002.
The Free Dictionary ""Ambient"" https://www.thefreedictionary.com/ambient, 3 pgs (Year: 2023).
Biology Online Dictionary ""Ambient Definition and Examples"" https://www.biologyonline.com/dictionary/ambient, 2 pgs (Year: 2022).

\* cited by examiner

DEVICE FOR ANALYSIS OF CELLULAR MOTILITY

CROSS-REFERENCE TO RELATED APPLICATIONS

This is a continuation application of U.S. patent application Ser. No. 16/929,791, filed 15 Jul. 2020, pending, and entitled DEVICE FOR ANALYSIS OF CELLULAR MOTILITY, which is a continuation application of U.S. patent application Ser. No. 14/888,700, filed 2 Nov. 2015, abandoned, and entitled DEVICE FOR ANALYSIS OF CELLULAR MOTILITY, which is a U.S. National Entry Application from PCT International Patent Application No. PCT/DK2014/050117, filed 2 May 2014, and entitled DEVICE FOR ANALYSIS OF CELLULAR MOTILITY, which claims the benefit of Danish Patent Application No. PA201370251, filed 3 May 2013, the disclosures of which are incorporated, in their entireties, by this reference.

TECHNICAL FIELD

This invention relates to a mesoscale fluidic system for analysing cellular motility in a sample, in particular the motility of cells in a sperm sample. The present invention also relates to a method of estimating the quantity and quality of motile cells in a sample and to a method of extracting motile cells from non-motile cells, in particular using the mesoscale fluidic system.

BACKGROUND

Awareness of decrease in male fertility potential has been high during the last decades, thus creating a demand for having sperm samples analysed. In particular, it is known that the concentration of motile sperm cells in a sample is the most predictive factor with regard to estimating the fertility of a sample (Tomlinson et al., 2013, *Human Fertility*, 1-19), At present an analysis for assessing the number and motility of cells in a sperm sample is typically carried out by professionals in a laboratory environment, and home diagnostic devices for estimating male fertility potential have only to a limited extent been addressed in the prior art. Such home diagnostic devices should preferably be simple to use, and they should be available at a low cost in order to be of a disposable nature without the need for auxiliary equipment such as microscopes, electrodes for impedance measurements or the like.

One device for testing a sperm sample in the comfort of the home environment is described in WO 2012/126478. WO 2012/126478 describes a mesoscale fluidic system capable of separating motile cells based on their motility and allowing detection and quantification of the cells. The system comprises a first analysis chamber in fluid communication with a further analysis chamber via a passageway, wherein the passageway has an entrance port in fluid communication with the first analysis chamber and an exit port in fluid communication with the further analysis chamber, wherein the cross-sectional area of the entrance port is larger than the cross-sectional area of the exit port. Each analysis chamber further comprises a solid-liquid separation unit defining an upstream surface facing the analysis chamber and a downstream surface facing an effluent channel, so as to allow fluid communication between the analysis chamber and the effluent channel via the solid-liquid separation unit. The connected analysis chambers allow motile cells to move from the first analysis chamber to the next, thus providing an estimate of the motility of cells in a sample.

WO 2012/126478 also describes an embodiment of the mesoscale fluidic system further comprising a cell permeable filter defining a sample application side opposite a conditioning medium side, wherein the cell permeable filter has a pore size allowing motile cells to swim through the filter. The cell permeable filter is said to minimise mixing of the liquid of a sample applied on the sample application side with a conditioning medium present at or added on the conditioning medium side. Thus, the cell permeable filter is provided to ensure that cells are not transported from the sample application side to the conditioning medium side via convection, so that cells present at the conditioning medium side will be motile cells that have traversed the cell permeable filter by swimming through it.

Some drawbacks with the prior art devices exist, which provide for a limited accuracy when estimating the number of motile cells. In particular, the presently available devices are not capable of sufficiently reducing contamination such as by immotile cells, even when cell permeable filters are integrated. This in turn means that immotile cells may be included in the estimates for cell motility. In addition, the migration of motile sperm cells through fluidic channels may decrease the concentration at the point of quantification to a level which is difficult to detect. This seems particularly true for systems comprising several serially connected analysis chambers.

It is therefore an object of the present invention to overcome these drawbacks and provide a mesoscale fluidic system having improved estimating accuracy, and at the same time complying with the requirements of a functional home diagnostic device.

SUMMARY

A first aspect of the present invention relates to a mesoscale fluidic system comprising a substrate having a sample chamber and an analysis chamber; the sample chamber comprising a cell permeable filter defining a sample application compartment and a conditioning medium compartment;

the sample chamber having a sample inlet port in the sample application compartment;
    the analysis chamber having an entry port and an exit port;
    the conditioning medium compartment being in fluid communication with the entry port of the analysis chamber via a channel;
    wherein the sample application compartment is below the cell permeable filter and the conditioning medium compartment is above the cell permeable filter.

The mesoscale fluidic system according to the present invention may be used for estimating the quantity of motile cells in a sample, in particular in a liquid sample. In general, a sample is added to the sample application compartment from which motile cells present in the sample will swim through the cell permeable filter into a conditioning medium present in the conditioning medium compartment. The liquid in the conditioning medium compartment may be moved to the analysis chamber, where the cells can be analysed, e.g. quantified. Since the motile cells are separated from non-motile cells which do not cross the cell permeable filter the cells quantified in the analysis chamber are motile cells.

For the present invention the manual "WHO laboratory manual for the Examination and processing of human semen" (fifth edition, World Health Organization, 2010, ISBN 978 92 4 154778 9) provides background information on sperm cells, and the manual is hereby incorporated by reference in its entirety.

The substrate may be made from any suitable material. The sample chamber may have any suitable shape or size with the proviso that the sample chamber can be divided into two separate compartments by the cell permeable filter. The cell permeable filter defines the conditioning medium compartment and the sample application compartment, and the cell permeable filter is thus considered to have a conditioning medium side and a sample application side facing the conditioning medium compartment and the sample application compartment, respectively. In an envisaged use of the system a conditioning medium is added to the conditioning medium compartment. The sample to be analysed is added to the sample application compartment. The order of adding the conditioning medium and the sample is not important although in a specific embodiment the sample is added to the sample application compartment before the conditioning medium is added to the conditioning medium compartment. Accordingly, the sample application compartment and the conditioning medium compartment may have any suitable size, respectively. The cell permeable filter defines the sample application compartment and the conditioning medium compartment by spanning across the sample chamber so that the only fluidic connection between the two compartments is through the cell permeable filter. The cell permeable filter may be of any appropriate design, material and shape, which allows the motile cells to be analysed to swim through the filter, thus allowing the cells to travel from the sample application compartment into the conditioning medium compartment. In particular, the cell permeable filter is selected with respect to the size and other characteristics of the cells to be separated, e.g. with respect to the size of the cells relative to the size of the pores of the cell permeable filter. The cell permeable filter, e.g. the pores of the cell permeable filter, may comprise a material to which the motile cells are attracted. The sample application compartment is below the cell permeable filter and the conditioning medium compartment is consequently above the cell permeable filter. The term "below" is to be viewed with reference to the gravitational field so that the force of gravity will be exerted in a direction from "above" to "below". The cell permeable filter may span the sample compartment in any suitable way, which provides for the sample compartment to be below the conditioning medium compartment.

The present inventors have surprisingly found that the effect of applying a cell permeable filter for separating motile cells from non-motile cells is significantly improved when the sample application compartment is below the cell permeable filter and the conditioning medium compartment is above the cell permeable filter. In another aspect the invention relates to a method of estimating the quantity of motile cells in a sample comprising the steps of: providing a cell permeable filter;

applying a sample containing motile cells below the cell permeable filter;

allowing motile cells in the sample to swim through the cell permeable filter;

detecting motile cells having swum through the filter. In yet a further aspect the invention relates to a method of extracting motile cells from non-motile cells comprising the steps of: providing a cell permeable filter;

applying below the cell permeable filter a sample containing motile cells and non-motile cells;

allowing motile cells in the sample to swim through the cell permeable filter;

extracting motile cells having swum through the filter. In general, all variations and embodiments described for any aspect of the invention is relevant for any other aspect of the invention, and the features of the embodiments may be combined freely.

The system or the methods of the invention may employ a cell conditioning medium, which is present or added below the cell permeable filter. A "cell conditioning medium" in the context of the invention is any liquid intended to support the cells in the sample, e.g. keep the cells viable, and it may for example contain nutrients, salts, buffers, and/or viscosity modifying agents as appropriate for the specific cells. Likewise, the system or the methods of the invention may employ a sample medium, which is present or added above the cell permeable filter. The "sample medium" may also contain nutrients, salts, buffers, and/or viscosity modifying agents as appropriate for the specific cells, and it may be the same as the cell conditioning medium, or the sample medium and the cell conditioning medium may be of different composition. In certain embodiments the cell conditioning medium and/or the sample medium may comprise a detection agent. In a certain embodiment the mesoscale fluidic system or the methods do not employ a sample medium.

Any suitable method for quantifying the motile cells may be applied in the system according to the present invention, and the analysis chamber may be of any suitable shape or size, which accommodates the selected method. The analysis chamber comprises an entry port and an exit port. In the context of the invention a "port" is any appropriate opening allowing fluid communication via the port. A port may be open by default, or it may be closed requiring opening via an actuator, such as a valve. The entry port provides access for the liquid, e.g. the conditioning medium containing the motile cells to the analysis chamber. The exit port allows the conditioning medium to exit the analysis chamber, and further a conditioning medium may also be applied to the conditioning medium compartment via the exit port of the analysis chamber. Likewise, the ports of the analysis chamber allow a fluid flow through the present mesoscale system. The entry port and exit ports may have any suitable design, which provides this functionality, and the ports may be in fluid communication with fluidic channels. In a specific embodiment, the sample inlet port is in fluid communication, e.g. via a channel, with a receiving well for receiving a sample, e.g. a sperm sample.

Accordingly, the system and the methods improve the separation of motile cells from non-motile cells in the sample, which motile cells may then be quantified in the analysis chamber, Mixing of the sample liquid with the conditioning medium is minimised when the sample application compartment is separated from the conditioning medium compartment by a cell permeable filter. The present inventors believe that while application of a cell permeable filter cannot fully prevent the convection of e.g. immotile cells from the sample application side to the conditioning medium side they have, however, observed a significant reduction in the convection across the cell permeable filter in a system according to the present invention, i.e. when the sample application compartment is below the conditioning medium compartment. In the context of the invention the term "convection" generally describes any passive transfer of mass, e.g. a situation where liquid components are carried along with the flow of a liquid. The present inventors believe that the reduced convection, and also diffusion, may, at least in part, be attributed to the gravitational force acting on the sample. That is, a downward force is exerted on all particles such as cells in the sample thereby limiting the passive movement in the upwards direction. Immotile cells having no means to counter the gravitational force are to a lesser extent transported by convection and diffusion up through the cell permeable filter. On the other hand motile cells having the means to actively transport themselves in any given direction in the liquid of the sample may easily overcome the gravitational force exerted on them, and by swimming transport themselves through the cell permeable filter. In particular, once motile cells encounter the cell permeable filter they tend to swim along the encountered surface thereby swimming through the cell permeable filter. Thus, the positioning of the sample below the cell permeable filter ensures to a higher extent that cells are not passively transported from the sample application side to the conditioning medium side via convection. Therefore, during an analysis of a sperm sample in the system according to the present invention the cells present on the conditioning medium side will be motile cells that have traversed the cell permeable filter by swimming through it. It is a further advantage of the present system that the distance which the motile cells will have to travel is short as compared to systems, wherein the motility is measured by the travelling distance of the cells in a channel. Thus, the shorter distance results in less time required for carrying out the analysis.

The present inventors have further observed that the mesoscale fluidic system and the methods of the invention further reduce contamination of the conditioning medium in the conditioning medium compartment. Samples such as sperm samples typically comprise additional particles, cells and molecules, which may also pass through the cell permeable filter and into the conditioning medium. However, applying the sample below the cell permeable filter also reduces the convection and diffusion of such additional components of the sample, which could otherwise lower the quality of the later analysis of the contents of the condition medium. In particular, a sperm sample, e.g. the sample liquid, may comprise enzymes that can have a negative effect on the analysis and therefore the separation of motile cells from the sample liquid housing such enzymes is especially advantageous.

Consequently, the present inventors have found that applying a sample with motile cells below a cell permeable filter, e.g. by providing a device having the sample application compartment below the cell permeable filter and the conditioning medium compartment above the cell permeable filter, results in a reduced contamination of the conditioning medium by immotile cells as well as additional contaminating components of the sample. It is ensured that only motile cells will enter the analysis chambers, which thus prevents immotile cells, debris and other components present in the sample to have a negative influence on the test result in the form of false positive and/or false negative contributions.

In an embodiment of the present invention the conditioning medium compartment further comprises a medium inlet port, which may be in fluid communication with the ambient. The medium inlet port may facilitate entry of a liquid, e.g. a sample conditioning medium containing components necessary for analysis of the cells, and furthermore the medium inlet port may provide a pressure release function since it may be in fluid communication with the ambient. The medium inlet port thereby ensures that sample in the sample application compartment is not actively transported through the cell permeable filter and into the conditioning medium compartment and/or analysis chamber when a negative relative pressure is applied via the exit port of the analysis chamber or when a positive relative pressure is applied via the medium inlet port, since the pressure drop over the cell permeable filter is significantly larger than the pressure drop over the medium inlet port. When liquid is loaded or withdrawn to or from the conditioning medium compartment either via the entry port of the analysis chamber or via the medium inlet port, the pressure exerted will be relieved through the opposite port. Accordingly, when the conditioning medium is loaded into the conditioning medium compartment through e.g. the entry port of the analysis chamber, the pressure exerted by any excess conditioning medium will be relieved via the medium inlet port. When conditioning medium is withdrawn from the conditioning medium compartment through the entry port of the analysis chamber the pressure is relieved by the medium inlet port, which thereby prevents suction of e.g. cells from the sample application chamber through the cell permeable filter. In a preferred embodiment of the present invention the analysis chamber comprises a cell retaining filter having an upstream surface facing the entry port and a downstream surface facing the exit port. The cell retaining filter may be of any appropriate design, material and shape, which allows for separating, e.g. retaining, cells from a liquid containing suspended cells when the liquid passes through the filter. The cell retaining filter spans across the analysis chamber so that the only fluidic connection between the entry and exit port of the analysis chamber is through the cell retaining filter. When a liquid in the conditioning medium compartment is withdrawn from the sample chamber, e.g. via an effluent channel in fluid communication with the ports of the analysis chamber, cells are retained on the upstream side of the cell retaining filter so that the cells are concentrated in the liquid in the analysis chamber or on the upstream surface of the cell retaining filter. This concentrating effect will allow that the motile cells in the sample, which have actively transported themselves into the liquid in the conditioning medium compartment (e.g. the conditioning medium), can be observed visually, e.g. on the upstream surface of the cell retaining filter. The result may also be visible on the downstream surface of the cell retaining filter. Alternatively, the cells may be suspended in a reduced volume of liquid remaining in the analysis chamber so that a higher concentration of the cells is provided in the analysis chamber compared to the concentration present in the liquid prior to withdrawal of liquid.

In a preferred embodiment the positioning of the cell retaining filter relative to the channel providing fluid communication between the conditioning medium compartment and the analysis chamber allows that the upstream surface and/or the downstream surface of the cell retaining filter is observed visually. For example, the channel for bringing the conditioning medium compartment in fluid communication with the entry port of the analysis chamber features a turn or the like so that observation of the upstream surface of the cell retaining filter requires observation along the channel through only the section of the channel between the turn and the cell retaining filter. Accordingly, the cell retaining filter can be observed directly and this also facilitates easy integration with optical detection.

In one embodiment of the present invention the analysis chamber is physically accessible. This allows for one or more cells to be removed from the analysis chamber and/or it allows for manipulation of cells already present in the chamber. The system may also be used to separate cells based on their motility with the intention to provide a subset of cells from a sample containing such cells. This is particularly useful for separating sperm cells of high motility from sperm cells of lower motility for use in Assisted Reproductive Technologies (ART). Thus, separation may be carried out in the system according to the invention and motile cells may be extracted from the analysis chamber.

In an embodiment of the present invention the mesoscale fluidic system further comprises means to provide a liquid driving force to move a liquid from the sample chamber to the analysis chamber and/or from the analysis chamber to the sample chamber. When the liquid is moved from the sample chamber to the analysis chamber the liquid may be a conditioning medium comprising motile cells. When the liquid on the other hand is moved from the analysis chamber to the sample chamber the liquid may be a conditioning medium. Any means suitable for providing a liquid driving force in the system may be applied.

In a preferred embodiment the means to provide a liquid driving force comprises a syringe. A syringe may easily be operated by e.g. pushing a button or by activating another actuator, and thus operation of a syringe requires minimal effort of the end-user. In addition, the mechanism of a syringe is a simple mechanical principle contributing to the overall robustness of the system. Movement of the piston in the cylinder of the syringe may also apply a liquid driving force in either direction through the mesoscale fluidic system, i.e. from conditioning medium compartment to analysis chamber or vice versa. Hence, a single syringe may be sufficient for both loading the system with conditioning medium and withdrawing sample through the system.

In one embodiment of the present invention the mesoscale fluidic system further comprises a sample medium, a conditioning medium and/or a detection agent. In other embodiments the sample medium, the conditioning medium and/or the detection agent may be added in use of the mesoscale fluidic system. In any case the system complies with the requirements of an easy-to-use home diagnostic device as it further reduces the risk of human error as fewer steps are required by the end-user. In a particular embodiment, the sample medium, sample conditioning medium and/or detection agent are supplied in one or more separate capsules, syringes or the like, or the appropriate components, e.g. a detection agent or components of the sample medium or cell conditioning medium, may be dried or coated directly in the system. A separate capsule or a syringe may be integrated in the mesoscale fluidic system or it may be external to the mesoscale fluidic system. Having the media and/or components of the media, e.g. detection agents, in separate capsules or syringes may improve the shelf-life of the mesoscale fluidic system as the individual media may be stored under optimal conditions.

Another aspect of the present invention relates to a method for estimating the quantity of motile cells in a sample and yet a further aspect relates to a method of extracting motile cells from non-motile cells as outlined above. In both methods a sample containing the motile cells is applied below the cell permeable filter; the sample containing motile cells may also contain non-motile cells from which the motile cells can be separated. In both methods a cell conditioning medium above the filter may be present or be added above the cell permeable filter, i.e. on the conditioning medium side, and a sample medium may be present or be added below the cell permeable filter. The cell conditioning medium and the sample application medium are as defined above. Any detection principle relevant for the mesoscale fluidic system of the invention is also relevant for any embodiment of the method aspect of the invention, and for any embodiment of the method aspects the cell permeable filter may be as for any embodiment of the mesoscale fluidic system. In specific embodiments the cell permeable filter is contained in a mesoscale fluidic system according to the invention. Any embodiment of the mesoscale fluidic system is relevant for both method aspects of the invention. When the mesoscale fluidic system is employed the method may further comprise the steps of: adding a conditioning medium to the sample chamber and the analysis chamber and the channel between them; optionally adding a detection agent to the sample chamber; adding the sample to the sample application compartment; allowing the motile cells of the sample to travel to the conditioning medium compartment; providing a liquid driving force from the sample chamber to the analysis chamber; quantifying the detection agent in the analysis chambers, e.g. on the cell retaining filter if present or extracting the motile cells from the analysis chamber. The mesoscale fluidic system may thus be prefilled with media, e.g. sample medium and/or cell conditioning medium, or these media may be applied to the mesoscale fluidic system during use.

The present inventors envisage a method for using the system according to the present invention, wherein a conditioning medium is initially provided in at least the conditioning medium compartment of the sample chamber. In certain embodiments the conditioning medium may be present in a reservoir or in the conditioning medium compartment of the sample chamber, when supplied to the end-user. A reservoir with a medium, e.g. sample medium and/or cell conditioning medium, or a detection agent will be in fluid communication with the appropriate chamber or compartment. In other embodiments the conditioning medium is added to the conditioning medium compartment through the analysis chamber or via the medium inlet port of the conditioning medium compartment, e.g. by use of a liquid driving force such as a syringe. Depending on the quantification method a detection agent may be added to the sample chamber. The detection agent may be an appropriate dye so that the motile cells may be dyed with the detection agent allowing detection and quantification of the population of cells in an analysis chamber from the intensity of the dye. The detection agent may also be a fluorescent dye so that cells may be quantified from measurement of a fluorescence signal as appropriate. The detection agent may be present in a reservoir or it may already be present in the sample chamber, e.g. it may be dried or coated directly in the system. A sample is then added to the sample application compartment, and a period of time is allowed for the motile cells of the sample to travel to the conditioning medium compartment. The conditioning medium is then pulled through the analysis chamber by means of a liquid driving force such as a syringe. The motile cells in the conditioning medium are retained in the analysis chamber, and the retained cells are quantified. If the motile cells are retained by a cell retaining filter a detection agent is typically used so that the cells can be quantified in the analysis chamber by visual means.

Accordingly, the above-mentioned methods, e.g. the method using the mesoscale fluidic system of the present invention, facilitate an accurate estimate of motile cells in a sample. Thus, it is possible for an end-user to obtain information about the motility of cells by carrying out the method on a sample in a home environment without prior experience and without any advanced technical knowledge.

The mesoscale fluidic system and the method aspects may be used for analysing the quantity and motility of motile cells in a sample or for separating motile cells based on their motility, e.g. for ART purposes, as appropriate. Motile cells may be prokaryotic cells, e.g. bacterial cells, or eukaryotic cells, such as yeast cells, amoebae, micro- and macro parasites and the like or motile mammalian cell types. A preferred cell type is sperm cells, in particular human sperm cells or other mammalian sperm cells, e.g. of household animals, such as cattle, horses, sheep, dogs, cats, etc.

In a further aspect the invention relates to a kit of parts comprising a mesoscale fluidic system according to any aspect of the invention, a detection agent, a sample medium and a cell conditioning medium. The detection agent, the sample medium or the cell conditioning medium may be present in the mesoscale fluidic system, e.g. in reservoirs or in the chambers, or they may be contained in containers separate from the mesoscale fluidic system. The kit may also comprise instructions for use of the kit. A preferred detection agent in the kit is a tetrazolium dye, such as MTT.

In a further aspect the invention relates to a system for analysis of motile cells in a sample, the system comprising a mesoscale fluidic system according to the first aspect of the invention and an external detector device comprising: an optical detector; a computer readable storage medium containing computer program code configured to quantify a detection agent in the analysis chambers or on the cell retaining filter of the mesoscale fluidic system, if present; a data processor for executing the computer program code.

In yet another aspect the invention relates to a mobile user terminal, e.g. a smart phone, containing computer program code configured to quantify a detection agent in the analysis chambers or on the cell retaining filter of a mesoscale fluidic system according to the first aspect of the invention, if present.

In yet another aspect the invention relates to a computer implemented method for determining a value of a quantifiable measure of cell motility for a cell sample comprising the steps of:

receiving image data comprising an image of at least a part of an analysis chamber and/or a cell retaining filter of a mesoscale fluidic system; and processing the image data to determine the value of the quantifiable measure wherein the step of processing the image data comprises the step of mapping the image data into the value of the quantifiable measure using a mapping function, the mapping function being calibrated to map image data of an analysis chamber and/or a cell retaining filter of a particular mesoscale fluidic system as disclosed in relation to the first aspect of the invention into a value of the quantifiable measure.

Consequently, a quantifiable measure may be determined automatically and operator independent.

All steps of the method may be performed on a single data processing system such as a user terminal e.g. a smart phone. The single data processing system may also be a stationary system, e.g. a clinical device. Alternatively, some of the steps may be performed on a remote computer server e.g. the step of processing the image data may be performed on a remote computer server.

The quantifiable measure may be an absolute measure e.g. the number of motile cells in the sample, a relative measure e.g. the percentage of motile cells in the sample. The quantifiable measure may also describe a state such as "good", "normal", "average", "low" etc. The WHO laboratory manual for the Examination and processing of human semen, Appendix 1, provides reference values for semen analyses, and Appendix 1 of the WHO laboratory manual for the Examination and processing of human semen is hereby incorporated by reference.

The calibration of the mapping function may be done by analysing the motility of a large number of samples using both the particular mesoscale fluidic system and traditional techniques e.g. manual microscope based techniques. Procedures for microscopic analysis of sperm cells are described in chapter 2, e.g. 2.7 and 2.8, of the WHO laboratory manual for the Examination and processing of human semen, which are hereby incorporated by reference.

In some embodiments, the method further comprises the step of pre-processing the image data to determine whether the image data is usable as input to the mapping function, wherein an error message is generated if it is determined that the image data is un-usable as input.

In some embodiments, the method further comprises the step of:

displaying the determined value of the quantifiable measure on a display.

In a further aspect the invention relates to a computer program product comprising program code means adapted to cause a data processing system to perform the steps of the computer implemented method disclosed previously, when the program code means are executed on the data processing system.

In some embodiments, the computer program product comprises a computer-readable medium having stored thereon the program code means.

A data storage medium may be a transportable medium such as a DVD, USB drive, or the like. Alternatively, a data storage medium may be a hard drive on a computer server connected to a computer network, e.g. the data may be stored via Internet services, such as Dropbox™, or using cloud storage.

In yet another aspect the invention relates to a device for determining a value of a quantifiable measure of cell motility for a cell sample, the device comprising a camera unit for capturing an image of a part of an analysis chamber and/or cell retaining filter of a mesoscale fluidic system, a processing unit for processing the captured image, a display for displaying the value of the a quantifiable measure of cell motility, and a user input unit, wherein, in response to activation of the user input unit;

the camera unit is configured to capture an image of a part of an analysis chamber and/or cell retaining filter of a mesoscale fluidic system; and the processing unit is configured to process the captured image to determine the value of the quantifiable measure of cell motility using a mapping function configured to map the captured image into the value of the quantifiable measure, wherein the mapping function is calibrated to map image data of an analysis chamber and/or cell retaining filter of a particular mesoscale fluidic system as disclosed in relation to the first aspect of the invention into a value of the quantifiable measure.

The camera unit may be any unit capable of collecting appropriate data of an image, e.g. a digital camera, a laser scanner, a CCD reader, a photodiode scanner or the like.

The display and the user input unit may be combined in a single unit e.g. in a touch screen.

In a particular embodiment the device comprises a housing chamber for housing the mesoscale fluidic device of the invention. The housing chamber may be set up to control the lighting conditions surrounding the mesoscale fluidic device, for example the housing chamber may shut out external light. The housing chamber may also be fitted with lamps, e.g. light emitting diodes, capable of providing light of a controlled composition, e.g. with respect to wavelengths, and intensity. The housing chamber may also be set up to define a specific distance between the mesoscale fluidic device and the camera unit, or the distance may be controlled, e.g. using a stage or the like.

In a further aspect the invention relates to a data storage medium comprising a computer readable code wherein said computer readable code is configured to programme a user terminal comprising a processing unit, a display, and a user input unit to become a device as specified immediately above.

A user terminal may be a smart phone or a tablet. The user terminal may also be a portable computer, e.g. a laptop computer, or a stationary computer. Thus, the computer readable code may be an application configured to programme the smart phone or tablet e.g. an Apple® IOS app, a Windows® Mobile App, and/or a Google® Android App. Alternatively, the computer readable code may be a web page configured to programme the user terminal e.g. a web app.

BRIEF DESCRIPTIONS OF THE DRAWINGS

In the following the invention will be explained in greater detail with the aid of examples of embodiments and with reference to the schematic drawings, in which FIG. 1 shows a schematic cross-section of the mesoscale fluidic system of the invention.

Figure 1:
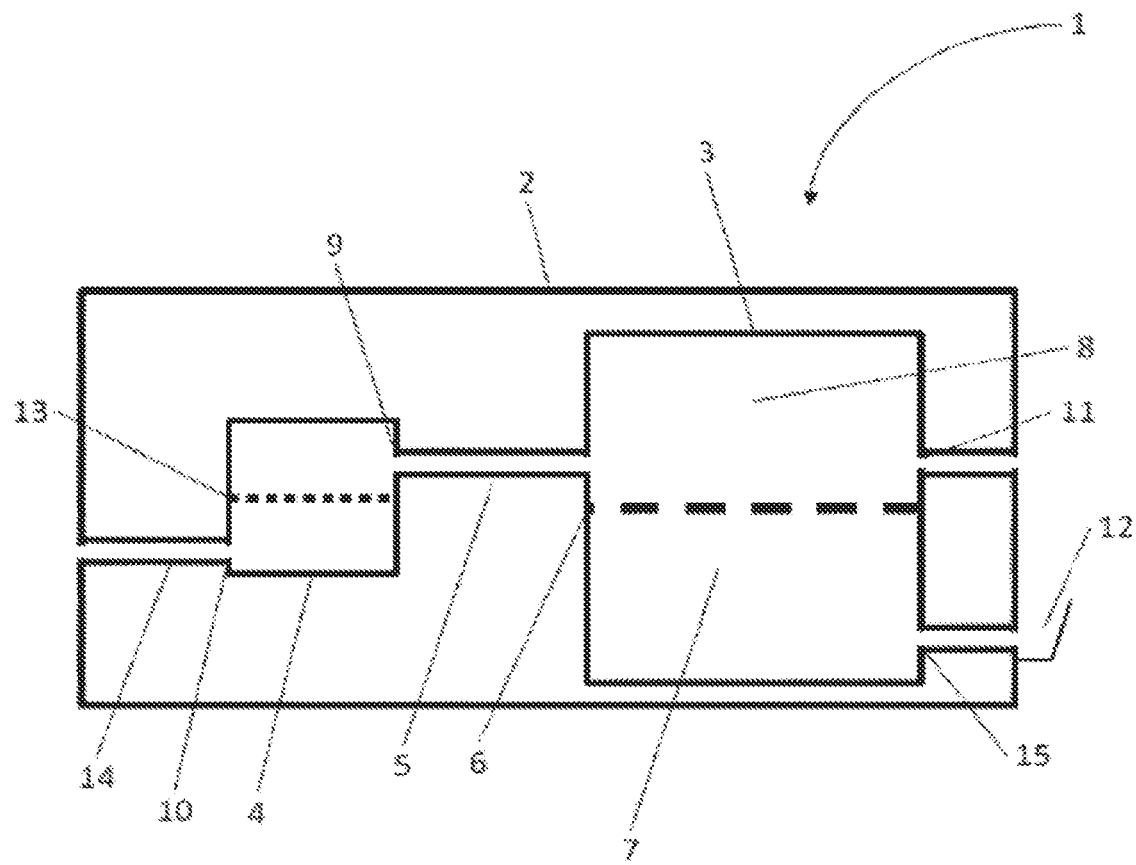

It should be understood that combinations of the features in the various embodiments are also contemplated, and that the various features, details and embodiments may be combined into other embodiments. In particular, it is contemplated that all definitions, features, details, and embodiments regarding the mesoscale fluidic system, the method of estimating the quantity of motile cells in a sample, and or the method of extracting motile cells from non-motile cells apply equally to one another.

Reference to the figures serves to explain the invention and should not be construed as limiting the features to the specific embodiments as depicted.

DETAILED DESCRIPTION

The present invention relates to a mesoscale fluidic system capable of separating motile cells based on their motility, e.g. of separating motile cells from non-motile cells and from the sample liquid, and to a method of estimating the quantity of motile cells in a sample and to a method of extracting motile cells from non-motile cells. This system may be used to analyse the content or quantity and also the motility of cells in a sample known or expected to contain motile cells. The system may also be used to separate cells based on their motility with the intention to provide a subset of cells from a sample containing such cells. This is particularly useful for separating sperm cells of high motility from sperm cells of lower motility for use in Assisted Reproductive Technologies (ART).

In the context of this invention the terms "motile" and "motility" refer to cells that are capable of moving in a liquid independently of any flow of the liquid, in particular, motile cells are capable of moving in non-flowing liquids. The motile cells may also be said to be "travelling" or "swim-ming" etc. Motility may be considered to be random, or cells may respond to a stimulus by swimming, e.g. by swimming towards or away from a given condition. Common stimuli may be for motile cells to move in response to a chemical gradient ("chemotaxis"), a temperature gradient ("thermotaxis"), a light gradient ("phototaxis"), a magnetic field line ("magnetotaxis"), or an electric field ("galvanotaxis"). Relevant stimuli will be known to the skilled person. In certain embodiments cellular motility may be induced by providing a stimulus relevant to a motile cell of interest in order to make the cell swim from its point of addition towards subsequent analysis chambers in the system. For example, a chemokine or other chemical may be placed in the conditioning medium compartment, e.g. in the conditioning medium, or the analysis chamber to attract motile cells added in the sample application compartment or to a receiving well.

In the context of this invention the term "mesoscale" is intended to cover a range of sizes where the smallest dimension of channels is in the range from about 10 µm to about 4 mm, e.g. about 100 µm to about 3 mm, typically about 2 mm, although the channels may also contain constrictions. Likewise a chamber may be of a depth of about 100 µm to about 20 mm or more, such as about 500 µm to about 2 mm, e.g. about 500 µm or about 1 mm, and the largest horizontal dimension may be from about 1 mm to about 50 mm, e.g. from about 1 mm to about 30 mm or from about 1 mm to about 20 mm, or from about 1 mm to about 10 mm, e.g. from about 2 mm to about 6 mm. The size of the receiving well, if present, should be sufficient to hold sample liquid to fill the sample application compartment of the sample chamber with fluid for analysis although it is also contemplated that the sample may be diluted in the receiving well in order to fill the sample application compartment. It can generally be said that fluids in mesoscale fluidic systems will be flowing under laminar conditions, and fluidic systems with channels or chambers different from those defined above may well be described as "mesoscale" as long as fluids contained in the systems flow under laminar conditions.

Referring now to the figures, a mesoscale fluidic system according to the present invention is depicted in FIG. 1, said mesoscale fluidic system 1 comprises a substrate 2 having a sample chamber 3 and an analysis chamber 4; the sample chamber comprising a cell permeable filter 6 defining a sample application compartment 7 and a conditioning medium compartment 8; the sample chamber 3 having a sample inlet port 15 in the sample application compartment 7; the analysis chamber 4 having an entry port 9 and an exit port 10; the conditioning medium compartment 8 being in fluid communication with the entry port 9 of the analysis chamber 4 via a channel 5; wherein the sample application compartment 7 is below the cell permeable filter 6 and the conditioning medium compartment 8 is above the cell permeable filter 6. The mesoscale fluidic system 1 may also comprise a receiving well 12 in fluid communication with the sample application compartment 7. The analysis chamber may comprise a cell retaining filter 13.

A "filter" according to the present invention is to be understood in the broadest terms as a unit capable of separating solids, e.g. cells, and liquid. Thus, the filter may be, e.g. a filter paper, a filter membrane etc., a sieve, a packed bed of particles. The present system comprises a cell permeable filter, which allows cells to traverse the filter, Optionally, the present system also comprises a cell retaining filter, which allows liquid to pass through and retains the cells. Accordingly, the two types of filters must feature different pore sizes depending on the cells to be analysed. The cell permeable filter 6 may have for example have a pore size from 1 μm to 20 μm, e.g. 1 μm to 3 μm, such as 1, 3, 5, 3, 10, 12, 15 μm etc., allowing motile cells to swim through it while at the same time providing a pressure drop across the filter. A preferred pore size is about 10 μm. In one embodiment the cell permeable filter 6 is a nucleopore filter, Appropriate materials for the cell retaining filter 13 may have a size cut-off of e.g., about 0.1 μm to about 20 μm, such as 0.1, 0.2, 0.3, 0.4, 0.5, 0.6, 0.7, 0.8, 0.9 or 1.0 μm although larger cut-off sizes may also be relevant, for example 1, 2, 3, 4, 5, 6, 7, 8, 9, 10 or 12 μm. Preferred cut-off sizes are 0.2 μm, 0.45 μm, 1 μm and 3 μm. In particular, the cut-off sizes of the cell permeable filter 6 and the cell retaining filter 13 are selected so that motile cells of interest can swim through the cell permeable filter 6 while being retained by the cell retaining filter 13. In one embodiment the cell retaining filter is a filter of mixed cellulose esters.

The mesoscale fluidic system of the invention is employed with a conditioning medium. The term "conditioning medium" is not intended to be limiting, but "conditioning" refers to it that the medium may contain components necessary for analysis of the motile cells and also for keeping the cells viable. Thus, the conditioning medium may contain pH buffers, salts, nutrients as appropriate to a cell type of interest. The conditioning medium may also contain a detection agent, or a detection agent may be added separately to a conditioning medium in the system or present in a dried form in a channel or chamber.

For detection and quantification the conditioning medium will typically comprise a detection agent. The detection agent may be or comprise a dye or a binding partner for a cell labelled with a dye, e.g. an antibody against a surface marker on the cell, which antibody is labelled with a dye or radioactive isotope or the like. Appropriate dyes may be fluorescent dyes or other dyes; a dye may be capable of binding specifically or non-specifically to a cell type of interest. Exemplary dyes for use as detection labels for quantifying sperm cells comprise Coomassie blue, Trypan blue, Crystalviolet, Nile blue, Nile red, Hematoxylin, Acid fuchsine, Eosin, Safranin, Nigrosin, Acridine orange, Giemsa, Erythrosin, Papanicolaou, Methylene blue, Neutral red, Phenol red, Hoechst stain, Resazurin, Bismarck Brown, tetrazolium dyes, Orange G, Periodic acid-Schiff, RoWright's stain, Jenner's stain, Leishman stain, Giemsa stain, Romanowsky stain, Sudan stain, propidium iodide and ethidium bromide. Preferred dyes are any tetrazolium dye, such as water soluble or water insoluble tetrazolium salts or compounds, e.g. 3-(4,5-dimethylthiazol-2-yl)-2,5-diphenyltetrazolium (MMT), 2-(4-iodophenyl)-3-(4-nitrophenyl)-5-phenyl-2H-tetrazolium (INT), e.g. as their bromide or chloride salts, 2,3-bis-(2-methoxy-4-nitro-5-sulfophenyl)-2H-tetrazolium-5-carboxanilide (XTT), 3-(4,5-dimethylthiazol-2-yl)-5-(3-carboxymethoxyphenyl)-2-(4-sulfophenyl)-2H-tetrazolium (MTS), 2,3,5-triphenyl-2H-tetrazolium (TTC), e.g. as a chloride salt, or Dimethyl tetrazolium. Tetrazolium dyes and their corresponding assays are well-known within the art. When the mesoscale fluidic system is employed for separating motile cells in a sample, e.g. to be used for ART, it is preferred that no dye or label is present. In specific embodiments two or more different detection agents are employed where additional detection agents can detect or quantify further characteristics of the motile cells, e.g. the two or more detection agents, e.g. different detection agents, may quantify two or more characteristics as appropriate for the detection agents, in particular two or more different characteristics. For example, appropriately labelled antibodies may be used as an additional detection agent in order to detect or quantify a specific surface antigen on the motile cells. Additional detection agents may also be employed as a negative control in order to ensure that a specific component is not present in the analysis chamber or on the conditioning medium side of the cell permeable filter. In general, any embodiment of the invention may employ two or more detection agents.

When several cell types are present in the sample, the detection agent can advantageously bind specifically and possibly also selectively to the cells of interest. It is preferred that the detection agent will change colour upon binding to specific cell types, e.g. live motile sperm cells. Thus, a preferred detection agent will not have a visible colour when not being bound to a cell, but upon binding to the cell it will change to have a detectable, e.g. visible, colour. It is preferred that the detection agent does not negatively affect the cells. In a preferred embodiment a conditioning medium containing a detection agent is contained in a reservoir, e.g. a receiving well, whereas the liquid in the analysis chambers and the passageways do not contain the detection agent. This will allow that the motile cells in the analysis chambers or on the surface of the cell retaining filter do not need to be washed for detection since the only detection agent in the analysis chambers has been carried there by the motile cells. Alternatively, a detection agent is added to the receiving well, containing a detection agent free conditioning medium, upon addition of sample. This will achieve the same effect. In yet another embodiment, in particular when the mesoscale fluidic system is not filled with a conditioning medium, a detection agent may be present in a dried form in a channel or chamber or in the cell permeable filter, or the detection agent may be present in the cell retaining filter or the mesoscale fluidic system may contain a detection agent absorbed in a pad or the like. For example, the detection agent may be coated onto a chamber or channel wall. Having the detection agent in a dried form will allow easy operation of the system by the end-user, since the detection agent will be present in a correct dosage and will be easily resolubilised upon application of sample conditioning medium. Unbound detection agent will typically be washed through the cell retaining filter whilst cell bound dye will be retained. In further embodiments, agents with specific functions may be present, e.g. in a dried form, in an analysis chamber or passageway.

In one embodiment the detection agent is a dye, which is dissolved in the conditioning medium, or is dried in the retaining filter and dissolved when conditioning medium is added to the system. In another embodiment the detection agent is a dye, which is placed in a compartment close to the medium inlet port 11 or the channel 5 in dried in form and dissolved when filling the conditioning medium compartment.

In use a sample containing motile cells is introduced into the sample application compartment 7 of the sample chamber 3, optionally through the receiving well 12. The cells are then allowed to travel to the conditioning medium compartment 8 of the sample chamber 3. The time allowed after addition of a sample will depend on the type of motile cells, but will typically be from about 10 minutes to about 1 hour, although shorter or longer times may also be used. When the system is used with sperm cells, the time allowed may constitute about 10, minutes, about 20 minutes, about 30 minutes, or about 40 minutes. When the time has been spent the conditioning medium may be withdrawn from the conditioning medium compartment 8 of the sample chamber 3 and the analysis chamber 4. The cells in the analysis chamber 4 may then be detected and/or quantified, or the cells may be withdrawn from the analysis chambers 4 using e.g. a pipette. Detection of motile cells on the cell retaining filter 13 or in the analysis chambers 4 may be performed simply by comparing the colour intensity observed, e.g. on the upstream surface of the cell retaining filter, and comparing this to an indication of the correlation between cell number and dye intensity, e.g. provided on the substrate 2 or from an optional control chamber.

The cell permeable filter 6 may further contain compounds, e.g. hyaluronic acid, attracting cells to the cell permeable filter 6 and to swim through it. The conditioning medium side will be connected to the analysis chamber 4. The cell permeable filter 6 may further minimise, or even prevent, mixing of the liquid of a sample applied on the sample application side with a conditioning medium present at or added on the conditioning medium side. Thus, the cell permeable filter 6 will ensure that cells are not transported from the sample application side to the conditioning medium side via convection or diffusion, so that cells present at the conditioning medium side will be motile cells that have traversed the cell permeable filter 6 by swimming through it.

The mesoscale fluidic system 1 of the invention comprises a substrate 2, which may be made from any convenient material, such as a polymer, a glass, a metal, a ceramic material or a combination of these. The substrate 2 is defined by a solid structure having a top and a bottom and a height suitable for comprising mesoscale fluidic structures such as chambers and channels. The chambers of the mesoscale fluidic structures may be open or closed, e.g. to the ambient, as found suited. For example, the ports defined above may be closable using e.g. valves, or the chambers may also comprise other openings. The chambers may be permanently closed at the top, or the system may feature any type of closable member, such as a sliding or hinged lid or a removable lid. Such means for access may apply to the whole of the system or to individual chambers and/or channels and/or structures. In this context the term "physical access", e.g. with respect to the analysis chamber 4 means that a tool may be inserted into the liquid in the analysis chamber 4 to manipulate the contents of the chamber 4. This manipulation may be to remove one or more cells from the analysis chamber 4, or it may involve manipulations of cells already present in the chamber 4. This type of physical access may also be provided for the sample chamber.

In one embodiment the substrate 2 has a shape most similar to a parallelepiped. The substrate 2 defines a bottom surface and one or more sidewalls of the sample chamber 3, analysis chamber 4 and the channel 5 between the chambers. All the structures are defined in the substrate 2. When the substrate 2 is viewed from above the sidewalls may form perimeters for each of the chambers defining their shape. Said shape may be round, square, polygonal, or oblong, etc. In a preferred embodiment the shape formed by the perimeter is round. Likewise, the channel 5 may have any convenient shape when viewed from above. If the substrate 2 is closed at the top the material used is preferably transparent. It is preferred that only a portion of the material is transparent allowing only observation of the relevant section of the system while the remaining material is opaque, e.g. white. The mesoscale fluidic system 1 of the present invention is preferably constructed from essentially transparent materials with hydrophilic surfaces, although well-defined regions of hydrophobic surfaces may also be used. In certain embodiments, the mesoscale fluidic system 1 may comprise sections of superhydrophilic surfaces to allow easy wetting of the sample chamber, analysis chamber and passageways with aqueous liquids. The mesoscale fluidic system 1 may also be constructed from non-transparent, e.g. white, materials. The construction material is preferably one or more thermoplastic polymers, although other materials, such as glass, silicon, metal, electromeric polymers, may also be used.

The sample chamber 3 may have any suitable shape with the proviso that the sample chamber 3 can be divided into two separate compartments 7,8. In a typical embodiment the sample chamber 3 is defined by a shape depressed into the substrate 2, wherein the body of the shape has at least a bottom base and at least a wall defining the hollow space of the sample chamber 3. The shape depressed in the substrate 2 is preferably truncated so that it does not go all the way through the bottom of the substrate 2. The shape of the sample chamber 3 may e.g. be cylindrical, frustoconical, cubic, rectangular parallelepiped, etc. In an embodiment of the present invention the sample chamber 3 is defined by a cylindrical shape depressed into the substrate 2, wherein the body of the cylindrical shape has parallel circular bases and a wall with a substantially constant circular cross-section, and wherein the circular bases are parallel to at least the bottom plane of the substrate 2. The sample chamber 3 may be open or closed at the top. In a specific embodiment, the sample chamber 3 is open to the ambient, e.g. upwards open, allowing addition of media and the like to the conditioning medium compartment 8; this embodiment may further comprise a cover for closing the sample chamber 3. The same may apply to the analysis chamber 4.

In an embodiment the sample chamber 3 is separated into compartments 7,8 by the cell permeable filter 6, wherein the cell permeable filter 6 defines a sheet-like cross-section spanning across the sample chamber 3, and wherein the cell permeable filter 6 is substantially parallel to at least the bottom plane of the substrate. In a certain embodiment, wherein the sample chamber 3 is defined by a cylindrical shape depressed into the substrate 2, the sample chamber 3 is separated into compartments 7,8 by a cell permeable filter 6, which defines a circular cross-section parallel to at least the bottom plane so as to form the shape of a disk dividing the sample chamber 3 into two compartments. In a specific embodiment the distance from the bottom, e.g. the "floor", of the sample chamber 3 to the cell permeable filter 6 is from about 100 µm to about 5 mm, e.g. about 4 mm or about 2 mm, thus defining the height of the sample application compartment 7, This embodiment is especially suited for analysing motile cells; in an embodiment for preparative purification of motile cells this distance may be larger, e.g. about 30 mm. The present inventors have found that the separation of motile cells from non-motile cells is particularly efficient when the height of the sample application compartment 7 is below 5 mm. It is believed that a height below 5 mm, e.g. 2 mm, improves the chance that a motile cell will encounter the surface of the cell permeable filter 6 and thereby be guided to swim across the cell permeable filter 6 and into the conditioning medium compartment. In a specific embodiment the sample application compartment has a depth of 4.4 mm and the conditioning medium compartment has a depth of 13.2 mm; the diameter of the sample chamber is 9.4 mm.

The sample application compartment 7 is below the cell permeable filter 6 and the conditioning medium compartment 8 is above the cell permeable filter 6. The present invention should be construed as to embrace any embodiment, wherein the general principle of providing a sample application compartment below a conditioning medium compartment, which compartments are separated by a cell permeable filter. That is, the sample chamber may be divided into compartments by a cell permeable filter, which spans the sample chamber 3 with an inclination with respect to the bottom of the device. It follows that the present inventors envisage that the cell permeable filter 6 may feature e.g. a part-spherical portion, which is either concave or convex with respect to either of the compartments 7,8. In another embodiment of the present invention the cell permeable filter 6 spans the sample chamber 3 substantially horizontally. When the distance from the bottom of the sample application compartment 7 to the cell permeable filter 6 is uniform, e.g. when both the bottom and the cell permeable filter are horizontal, an improved separation of motile cells from non-motile cells has been observed, in particular when the distance between the sample application compartment 7 and the cell permeable filter 6 is below 5 mm.

The sample chamber 3 should have a suitable volume for holding a sample in the sample application compartment 7 and a conditioning medium in the conditioning medium compartment 8. A person skilled in the art would readily know the dimensions required for the sample chamber 3 to contain the sample. The sample application compartment 7 and the conditioning medium compartment 8 may be of approximately equal volumes, although the sample application compartment is typically larger, e.g. 2 to 5 times larger, than the conditioning medium compartment. These ratios are particularly relevant for analysis of motile cells. For preparative purification of motile cells the ratio may be even larger.

The sample inlet port 15 should be construed in a broad sense as a means for placing the sample in the sample application compartment 7, The sample is placed below the cell permeable filter 6, in a preferred embodiment the sample inlet port 15 comprises a channel providing fluid communication from the outside and into the sample application compartment 7 of the sample chamber 3. The mesoscale fluidic system 1 may advantageously also comprise a receiving well 12 in fluid communication with the sample inlet port 15. The present inventors also envisage alternative means for placing the sample inside the sample application compartment 7. Alternatively, the receiving well 12 may be in the form of a drawer or the like having a sample application location allowing fluid communication with the ambient and a sample analysis location allowing fluid communication with the sample application compartment 7. For example, when the receiving well is in the ambient location a sample may be added to the receiving well. When the receiving well, e.g. containing a sample, is moved to the sample analysis location the receiving well be in fluid communication with the sample application compartment 7 but no longer with the ambient.

In a preferred embodiment the device 1 comprises a receiving well 12 in fluid communication with the sample inlet port 15. The receiving well 12 will provide a location for adding a sample to be analysed.

In a preferred embodiment the positioning of the cell retaining filter 13 relative to the channel providing fluid communication between the conditioning medium compartment and the analysis chamber allows that the upstream surface and/or the downstream surface of the cell retaining filter is observed visually. For example, the substrate 2 or the cover, when used, may be transparent meaning that the contents of an analysis chamber 4 may be observed, e.g. with the naked eye or using a microscope or the like. However, in addition to being transparent to visible light the substrate 2 or the cover may also be transparent to other wavelengths, such as ultraviolet light or infrared light. Transparency to ultraviolet light allows that certain fluorescent molecules, e.g. dyes or labels, can be excited with an appropriate light source. The remaining substrate 2 may likewise be transparent. The substrate 2 and the cover may have the same or different characteristics regarding transparency. However, in certain embodiments the substrate 2 may comprise filters to ranges of wavelengths to aid in excitation and observation of fluorescent dyes. For example, one part of the substrate 2 may be transparent to an excitation wavelength but not the emission wavelength and another par may in turn be transparent to the emission wavelength but not the excitation wavelength. In certain embodiments the substrate 2 or the cover above the analysis chamber 4 comprises a magnifying lens. This will allow easier observation of the contents of an analysis chamber 4 and preferably also the cell retaining filter 13. Magnifying lenses are well-known to the skilled person.

In an embodiment of the present invention the mesoscale fluidic system 1 further comprises means to provide a liquid driving force to move a liquid from the sample chamber 3, in particular the conditioning medium compartment 8, to the analysis chamber 4 or from the analysis chamber 4 to the sample chamber 3. A liquid driving force may be provided by applying a positive relative pressure to the medium inlet port 11 to disperse the liquid into the analysis chamber 4 from the conditioning medium compartment 8. Alternatively, a negative relative pressure applied to the effluent channel 5 from the analysis chamber 4 via the exit port 10 will create the same effect, i.e. move liquid from the conditioning medium compartment 8 of the sample chamber 3 to the analysis chamber 4 and further withdraw liquid from the analysis chamber 4 via the cell retaining filter 13, when present. Essentially all liquid may be withdrawn from the analysis chamber 4 to concentrate the motile cells present in the analysis chamber 4 on the surface of cell retaining filter 13 allowing detection of the cells. The means to provide a liquid driving force may be integrated into or be external to the mesoscale fluidic system 1.

In a preferred embodiment the means to provide a liquid driving force comprises a syringe. A syringe allows easy operation of the device 1 by the end-user without requiring auxiliary pumps or the like. A syringe is preferably designed to be operable manually. The syringe may have a piston with predefined settings, to aid the user in operating the device. For example, the syringe may have two settings with a first setting defining a "start position" and a second setting defining an "end position". In an embodiment a sample is applied in the receiving well 12 with the conditioning medium compartment 8 being filled with conditioning medium; in this case the piston of the syringe is in the start position; moving the piston to the end position will create a driving force to move the liquid from the conditioning medium compartment 8 via the analysis chamber 4 through the cell retaining filter 13 and into the effluent channel 5. Alternatively the syringe may contain the conditioning medium and moving the piston from the start position to the end position can fill the conditioning medium compartment 8. After application of the sample to the receiving well 12 or to the sample application compartment 7, returning the piston from the end position to the start position will create a liquid driving force from the conditioning medium compartment 8 via the analysis chamber 4 through the cell retaining filter 13 and into the effluent channel 5. The piston may also have more than two predefined settings with intermediate settings between the start and the end positions corresponding to various stages of the operation of the device 1.

Other means of providing a liquid flow in the device are also possible. For example, in the form of a peristaltic function acting on the effluent channel. Alternatively, the system may be connected to an external auxiliary pump or a vacuum container.

In one embodiment of the present invention the mesoscale fluidic system 1 further comprises a sample medium, a conditioning medium and/or a detection agent. Accordingly, in a particular embodiment the mesoscale fluidic system 1 is prefilled with conditioning medium. The conditioning medium may be present in the analysis chamber 4, the sample chamber 3, in particular the conditioning medium compartment 8, and passageways 5,14. The mesoscale fluidic system 1 may also comprise separate reservoirs for sample conditioning medium and/or a detection agent. The mesoscale fluidic system 1 may also comprise several separate reservoirs when different reactants are required at different stages of analysis of motile cells. The reservoirs are in fluid communication with the sample chamber 3, in particular the conditioning medium compartment 8, or the analysis chamber 4 as appropriate, i.e. the conditioning medium may be applied to the system 1 via either chamber or compartment. In an embodiment of the present invention, the sample conditioning medium is supplied in a separate capsule, syringe or the like. In such an embodiment the mesoscale fluidic system 1 may comprise a separate channel with an external fluid application port, which channel is in direct fluid communication with the analysis chamber 4 or the sample chamber 3, in particular the conditioning medium compartment 8. The external fluid application port may, however, be the exit port 10 of the analysis chamber 4 or the medium inlet port 11 of the conditioning medium compartment 8, A capsule and the external fluid application port may be fitted with complementary connection devices. The capsule may be made from a flexible material allowing adjustment, e.g. reduction, of the volume to inject the contents of the capsule into the fluid application port. If the conditioning medium is contained in a reservoir it may be in fluid communication with either the conditioning medium compartment 3 of the sample chamber 3 or the analysis chamber 4 via a channel or the like. Such a channel may comprise a valve or a membrane or similar structure preventing a flow in the channel until the valve or membrane is activated to allow a flow. This will ensure that premature entry of the conditioning medium into the chambers is prevented. For example, an actuator may allow opening of the channel for flow of liquid from the reservoir to the sample chamber 3, in particular the conditioning medium compartment 8. Thus, in one embodiment a sample conditioning medium is initially contained in a reservoir, whereas the sample chamber 3 and analysis chamber 4 do not contain liquid. Upon opening of the channel to flow, the conditioning medium will flow from the reservoir into the sample chamber 3 and the analysis chamber 4. Once the conditioning medium compartment 8 of the sample chamber 3 and the analysis chamber 4 contain liquid, motile cells may travel from the sample application compartment 7 to the conditioning medium compartment 8. In an alternative embodiment the analysis chamber 4 may be provided with a liquid, which may be the same liquid present in a reservoir or a different liquid. In yet another embodiment, no liquids are provided in the mesoscale fluidic system 1 but added to the system before analysis of a sample.

The downstream surface of the cell retaining filter 13 may be in fluid communication with an effluent channel 14. The mesoscale fluidic system 1 preferably comprises only a single effluent channel 14 allowing that a single means to provide a liquid driving force, e.g. a pump or a syringe, may be employed to withdraw liquid from the sample chamber 3 and analysis chamber 4, The effluent channel 14 will be of mesoscale dimensions so that liquid flow in the effluent channel 14 will be laminar as defined above. Typically, the diameter of the effluent channel 14 will be from about 500 µm to about 3 mm, e.g. about 1 mm. In general, it is desirable that the diameter of the effluent channel 14 does not introduce an excessive pressure drop in the channel so that liquid from the sample chamber 3 and analysis chamber 4 may be easily withdraw using simple means, e.g. a syringe.

In a certain embodiment the mesoscale fluidic system 1 comprises a means to regulate the temperature, in particular to increase the temperature over typical ambient temperature, Appropriate means to regulate temperature may thus comprise a heating element, such as a coil of an electrically conductive wire, a Peltier element, tubes for a heating and/or cooling liquid, or similar. It is noted that a Peltier element may also be used to cool the system if desired.

Channels, chambers, passageways and other structures of the mesoscale fluidic system 1 of the present invention may be formed by joining a first substrate comprising structures corresponding to the channels and chambers with a second substrate. In the following, such features are generally referred to as "channels and chambers" although this should not be considered limiting, Thus, the channels and chambers may be formed between two substrates upon joining the substrates in layers. The mesoscale fluidic systems are not limited to two substrate layers. In certain embodiments multiple substrate layers may be used where each of the substrate layers may comprise structures for channels and chambers as appropriate. In particular, the cell permeable filter 6 and the cell retaining filter 13 may each be contained in a single layer, and likewise the channels 5, 14 may each be formed between two substrate layers. These multiple substrate layers are then joined so as to be assembled as a mesoscale fluidic system 1.

The structures corresponding to the channels and chambers in the substrate may be created using any appropriate method. In a preferred embodiment the substrate materials are thermoplastic polymers, and the appropriate methods comprise milling, micromilling, drilling, cutting, laser ablation, hot embossing, injection moulding and microinjection moulding, and 3D printing. These and other techniques are well known within the art. The channels may also be created in other substrate materials using appropriate methods, such as casting, moulding, soft lithography etc. It is also possible to employ different types of materials, e.g. thermoplastic materials, glasses, metals etc. to make a single mesoscale fluidic system. The substrate materials may be joined using any appropriate method. In a preferred embodiment the substrate materials are thermoplastic polymers, and appropriate joining methods comprise gluing, solvent bonding, clamping, ultrasonic welding, and laser welding. Other relevant methods are fixing with screws or other fastening means.

In another embodiment of the present invention the mesoscale fluidic system comprises a substrate having a sample chamber and two or more analysis chambers; the sample chamber comprising a cell permeable filter defining a sample application compartment and a conditioning medium compartment; the sample chamber having a sample inlet port in the sample application compartment; the two or more analysis chambers each having an entry port and an exit port; wherein the sample application compartment is below the cell permeable filter and the conditioning medium compartment is above the cell permeable filter, and wherein the conditioning medium compartment comprises one or more additional cell permeable filter(s) defining two or more sub-compartments of the conditioning medium compartment 8, and wherein each of the two or more sub-compartments of the conditioning medium compartment 8 is in fluid communication with an entry port of a corresponding analysis chamber via a channel. In a preferred embodiment the one or more additional cell permeable filter(s) span the sample chamber in a plane parallel to the first cell permeable filter 6, which defines the sample application chamber 7 and the conditioning medium chamber 8. The one or more additional cell permeable filter(s) defines at least two sub-compartments of the conditioning medium compartment 8, thus creating a series of sub-compartments on top of each other. The motile cells may then travel from the sample application compartment 7 into the first sub-compartment of the conditioning medium compartment 8, the serially connected sub-compartments further allow motile cells to move from the first sub-compartment to the second and on to the third, etc. The motile cells having the highest motility will travel into further sub-compartments and the cells accumulated in each sub-compartment may then be detected in the respective analysis chamber connected to the respective sub-compartments. The motility of the population of cells may then be estimated from the number of cells in each analysis chamber. Accordingly, the estimate of motile cells is broken down into additional fractions of motility. In certain embodiments the mesoscale fluidic system 1 may have more than three sub-compartments of the conditioning medium compartment 8 and corresponding number of analysis chambers, for example the mesoscale fluidic system 1 may have 3, 4, 5, 6, 7, 8, 9 or 10 or even more sub-compartments and analysis chambers.

In another embodiment of the present invention the mesoscale fluidic system comprises a further analysis chamber for parallel estimation of the total cell count. The further analysis chamber may be designed similar to the analysis chamber for analysing motile cells. In an embodiment the further analysis chamber comprises an entry port and an exit port. The further analysis chamber may be in fluid communication through the entry port via a channel with the sample application compartment. The further analysis chamber may alternatively be in fluid communication through the entry port via a channel with an additional sample chamber, wherein the sample chamber 3 and the additional sample chamber may optionally be in fluid communication with the same receiving well 12.

In one embodiment of the mesoscale fluidic system 1 the receiving well 12, the analysis chamber 4, and the passageways are covered with a cover, and where at least the part of the cover, which is covering the analysis chamber 4, is transparent. In another embodiment the mesoscale fluidic system the transparent part of the cover constitutes a smart phone software application readable display.

In a further aspect the invention relates to a system for analysis of motile cells in a sample, the system comprising a mesoscale fluidic system according to the first aspect of the invention and an external detector device comprising: an optical detector; a computer readable storage medium containing computer program code configured to quantify a detection agent in the analysis chamber or on the cell retaining filter of the mesoscale fluidic system, if present; a data processor for executing the computer program code. The external detector device may further comprise a display for presenting quantification results to an operator. For example, the results may be presented as a table with the estimated quantity of cells in each analysis chamber presented as an absolute quantity or as a relative quantity, e.g. of the relative distribution of cells in the analysis chambers, or the result may be presented as an overall result to describe the sample, e.g. the sample may be described as "good", "normal", "average", "low", etc. The optical detector may be any detector capable of reading the results from the mesoscale fluidic system, e.g. quantifying the detection agent on the cell retaining filter. Particularly useful optical detectors are those used for scanning barcodes or the like, and in a certain embodiment the optical detector is selected from the group consisting of a camera, a laser scanner, a CCD reader, a photodiode scanner or the like. In a preferred embodiment the external detector device is a mobile user terminal. With "mobile user terminal" is meant any portable computing device, such as a mobile telephone, smart phone, personal digital assistant, portable computer, tablet computer or the like. The mobile user terminal is preferably a computing device employing Apple iOS, Android, Symbian, Windows Phone or similar operating systems.

A further aspect of the invention relates to a mobile user terminal, e.g. a smart phone, containing computer program code configured to quantify a detection agent on the cell retaining filter of a mesoscale fluidic system according to the first aspect of the invention.

In an embodiment, the quantification of motile sperm cells is performed by using a smart phone as an external detector device. In this embodiment the receiving well, the analysis chamber, and the passageways of the mesoscale fluidic system are covered with a cover, where at least the part of the cover covering the analysis chambers is transparent and constitute a smart phone readable display. By using a smart phone provided with a digital camera, and computer program code, e.g. an app, enabling the smart phone to prosecute data obtained by the camera, the display can be read and data for the purpose of quantification and qualification (motility) of motile sperm cells can be obtained, and thereby give the user of the smart phone an indicative value of result, e.g. in terms of the concentration and motility of the sperm cells. The data can be stored in the smart phone and used to compare with data from prior tests. In a particular embodiment the computer program code is configured to upload the results to a database to allow comparison with results in the database, e.g. from other users or from prior tests. Data uploaded to the database may be stored in the database for future comparison.

An embodiment of the present invention relates to the use of the mesoscale fluidic system, wherein the loading of the sperm sample comprises the steps of: 1) collecting a sperm sample in a sperm collecting cup; 2) transferring the sperm sample from the sample cup to a mesoscale fluidic system according to the present invention by suitable means such as using a Pasteur pipette.

Figure 2:
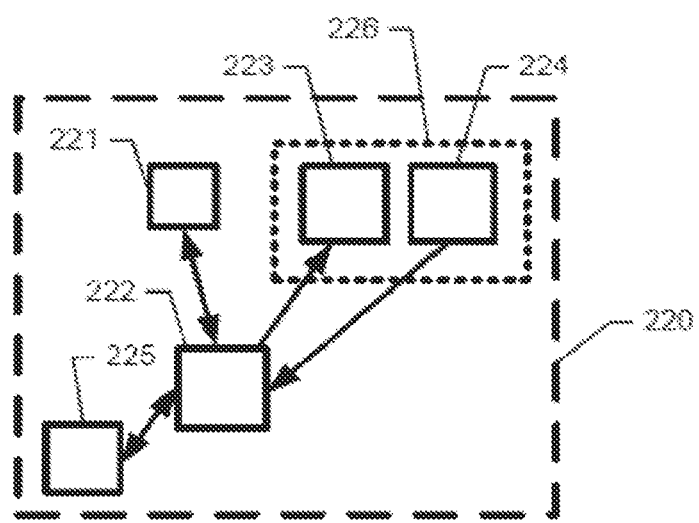
FIG. 2 shows a schematic drawing of a device for determining a value of a quantifiable measure of cell motility for a cell sample, according to an embodiment of the invention.

FIG. 2 shows a schematic drawing of a device 220 for determining a value of a quantifiable measure of cell motility for a cell sample, according to an embodiment of the invention. The device 220 comprises a camera unit 221 for capturing an image of a part of an analysis chamber and/or a cell retaining filter of a mesoscale fluidic system, a processing unit 222 for processing the captured image, a display 223 for displaying the value of the a quantifiable measure of cell motility, and a user input unit 224. In response to activation of the user input unit 224;

the camera unit 221 is configured to capture an image of a part of the analysis chamber and/or the cell retaining filter of the mesoscale fluidic system; and the processing unit 222 is configured to process the captured image to determine the value of the quantifiable measure of cell motility using a mapping function 225 configured to map the captured image into the value of the quantifiable measure. The mapping function 225 is calibrated to map image data of an analysis chamber and/or a cell retaining filter of a particular mesoscale fluidic system of the invention into a value of the quantifiable measure.

The display 223 and the user input unit 224 may be combined in a single unit e.g. in a touch screen 226.

To determine a value of the quantifiable measure of cell motility for a particular cell sample, a mesoscale fluidic system of the invention comprising the sample may be arranged in proximity of the device 220, This may be achieved by arranging the device 220 and the mesoscale fluidic system in a common alignment unit. Alternatively, the device 220 may be held by hand above the mesoscale fluidic system with the camera unit pointing towards the analysis chamber and/or cell retaining filter of the mesoscale fluidic system. Next, in response to activation of the user input unit 224, the camera unit 221 captures an image of a part of the analysis chamber and/or cell retaining filter of the mesoscale fluidic system, and the processing unit 222 process the captured image to determine the value of the quantifiable measure of cell motility.

This allows the visual output of the mesoscale fluidic system to be analysed automatically. This may improve the precision, especially when the mesoscale fluidic system is used for self testing, i.e. when the user is not a professional health care provider.

In an embodiment of the present invention the sperm collecting cup is an integrated part of the device. The sperm collecting cup may after ejaculation be connected to the device and thereby loading the sperm sample. In another embodiment of the present invention the sample application compartment 7 comprises means to ensure a precise sample volume is provided in the system to give more accurate results. In a certain embodiment the means to ensure a precise sample volume is an over float system.

Example 1

Experiments were conducted to compare the effect of having the sample application compartment below the cell permeable filter and the conditioning medium compartment above the cell permeable filter with previous applications of cell permeable filters, where the sample application compartment is e.g. beside or above the conditioning medium compartment.

A comparison between having sample application compartment above and below the cell permeable filter was carried out.

A semen sample containing only immotile cells was used. The sample was then split into two samples for testing.

Sample Application Compartment Above a Cell Permeable Filter

One sample was applied to a system having a sample application compartment above a cell permeable filter and a conditioning medium below the filter. The conditioning medium was pipetted into the conditioning medium compartment and the semen sample was pipetted into the sample application compartment. A sample of conditioning medium was extracted and analysed in the time interval provided in Table 1 below.

TABLE 1

| Time | Cell count (millions/ml) |
|---|---|
| 5 min | 0.1 |
| 10 min | 0.7 |
| 15 min | 0.7 |

Evidently, the results show that immotile cells have traversed the cell permeable membrane, and the present inventors attribute this result to the effect of the gravitational force.

Sample Application Compartment Below a Cell Permeable Filter

The second part of the sample was applied to a system having a sample application compartment below a cell permeable filter and a conditioning medium above the filter. The conditioning medium was pipetted into the conditioning medium compartment and the semen sample was pipetted into the sample application compartment. A sample of conditioning medium was extracted and analysed in the time interval provided in Table 2 below.

TABLE 2

| Time | Cell count (millions/ml) |
|---|---|
| 5 min | 0 |
| 10 min | 0 |
| 15 min | 0 |

The present inventors found that no cells had traversed the cell permeable filter when the sample was placed below the filter.

Example 2

The dynamic range of the colour intensity of the RGB values of image data for an image from a mesoscale fluidic device of the invention was correlated with the manual count of a titrated semen sample. A semen sample containing 185 million motile sperms per milliliter was diluted 2-fold serially with semen plasma. The samples were applied to the test devices using standard incubation parameters using MU at a concentration of 0.5 mg/ml as a detection agent. Photographs of the results were taken with a Microsoft life digital camera and the colour intensities (RGB values) measured. The mesoscale fluidic device comprised a cell retaining filter, and for each image for analysis the mesoscale fluidic device was placed in a light box to ensure the same conditions at all times. The light box consisted of a box and included the camera positioned approximately 55 mm from the object and a 12 volt halogen bulb. The camera attributes were controlled by a custom made Labview program. Conditions at which the test have been conducted were: Temperature: 20° C.±1.5° C., humidity: 38% RH.

Figure 3:
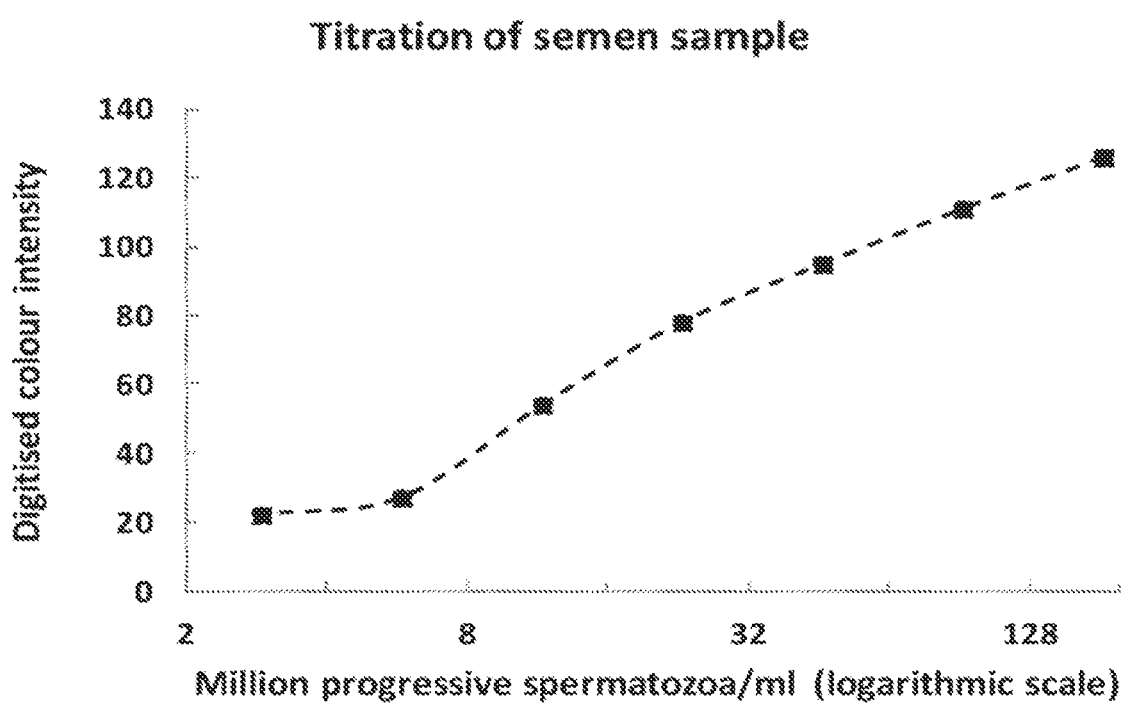
FIG. 3 shows data for titration of a semen sample.

The results are shown in FIG. 3, which shows the dynamic range of titration curve obtained. There is a linear relationship between the colour intensity and the log, concentration of motile sperms in the samples. The colour intensity of the spots in the test device is highly correlated to the number of motile sperms present in the samples both measured by the optical analysis and manual by the eye.

Example 3

The possible effects of two detection agents, MTT and crystal violet, on the motility of sperm cells were tested.

Stock solutions of MTT and crystal violet of 5 mg/ml and 1 mg/ml, respectively, were prepared, and these were diluted two-fold serially. The detection agent solutions were mixed with sperm samples comprising 60 million motile cells per milliliter and 72 million cells per milliliter in total (denoted 60/72) in a 50:50 ratio and the mixtures were incubated for 60 min at ambient temperature before analysing the cells microscopically.

TABLE 3

| MTT (mg/ml) | Cells | Crystal violet (mg/ml) | Cells |
|---|---|---|---|
| 0 | 60/72 | 0 | 60/72 |
| 5 | 18/64 | 1 | 40/63 |
| 2.5 | 30/63 | 0.5 | 27/43 |
| 1.25 | 34/65 | 0.25 | 32/56 |
| 0.625 | 48/77 | 0.125 | 37/56 |

It is evident from Table 3 that MTT had an effect on the cellular motility. The ratio of motile versus non-motile cells (% motile) was lowered at the higher concentrations, whereas the ratio was not affected by crystal violet. However, at MTT concentrations below 2.5 mg/ml no effect on motility was observed (not shown). Thus, both detection agents may be used and within the standard conditions, e.g. incubation time <30 min, 0.5 mg/ml for MU, no effects on motility are observed. It is noted that these effects are only relevant in embodiments where the detection agent is mixed with the sample prior to allowing the cells to migrate through the cell permeable filter.

Example 4

A mesoscale fluidic device of the present invention was tested with sperm samples. The system comprised a cell permeable filter of 13 mm diameter and a pore size of 10 µm. The thickness of the cell permeable filter was 10 µm. The volume of the sample application compartment was approximately 600 µl and the distance from the bottom of the sample application compartment to the cell permeable filter was 4.25 mm. A sample cup was in fluid communication with the sample application compartment. A sperm sample was applied to the sample cup resulting in a sample volume of 600 µL entering the sample application compartment. After application of the sample a conditioning medium (comprising 0.5 nag/ml MTT) was injected, using a syringe, via the exit port of the analysis chamber through the cell retaining filter and into the conditioning medium compartment (of a volume of 300 µl). The device was incubated for 30 min. After incubation the syringe was used to withdraw liquid, now including the motile cells, from the sample application compartment in order to capture the motile cells on the cell retaining filter.

Figure 4:
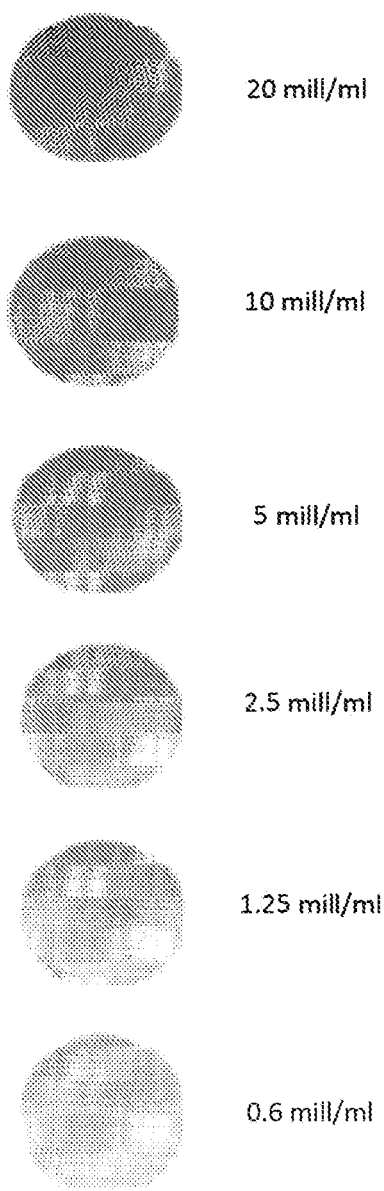
FIG. 4 shows photos of cell retaining filters of a mesoscale fluidic device of the invention after use.

The tests were performed using samples prepared from a semen sample where the concentration of motile cells was quantified microscopically and diluted to contain cells in the range of from 0.6 million per milliliter to 20 million per milliliter. Photos of cell retaining filters from the devices are shown in FIG. 4, which shows that within the concentration range 5 million motile cells per milliliter could easily be differentiated from lower concentrations.

Example 5

The mesoscale fluidic device of the invention was tested against a commercial test strip assay known as SpermCheck. SpermCheck claims to differentiate above or below 20 million total spermatozoa/ml whereas the present device has a cut-off value of 5 million progressive sperm cells (WHO 2010 criteria, WHO laboratory manual for the Examination and processing of human semen). Specifically, the purpose of the test is to have lay men placing test results generated by the mesoscale fluidic device of the invention into two categories "poor" or "normal". 45 sperm samples were obtained and analysed microscopically before applying all samples to mesoscale fluidic devices of the invention or to SpermCheck test strips. After the analyses all devices and test strips were photographed and the photos included in a presentation to 5 different people (2 university students from SDU and 3 engineers from 2C Engineering company; in Table 4 and Table 5 below the subjects are referred to as A to E) who were instructed to classify the photos according to the categories "low" and "normal". The same treatment was performed by an internal person (denoted "Control"). Table 4 and Table 5 show the results of the experiment.

TABLE 4

| Invention | A | B | C | D | E | Average | Control |
|---|---|---|---|---|---|---|---|
| Sensitivity (%) | 75 | 71 | 75 | 80 | 79 | 76 | 88 |
| Specificity (%) | 89 | 89 | 84 | 89 | 89 | 88 | 84 |
| PPV (%) | 90 | 89 | 86 | 91 | 90 | 89.2 | 88 |
| NPV (%) | 74 | 71 | 73 | 76 | 77 | 74.2 | 84 |

TABLE 5

| SpermCheck | A | B | C | D | E | Average | Control |
|---|---|---|---|---|---|---|---|
| Sensitivity (%) | 51 | 41 | 69 | 79 | 56 | 59.2 | 51 |
| Specificity (%) | 100 | 100 | 100 | 75 | 100 | 95 | 100 |
| PPV (%) | 100 | 100 | 100 | 97 | 100 | 99.4 | 100 |
| NPV (%) | 17 | 15 | 25 | 27 | 43 | 25.4 | 17 |

The lay user test results were close to the results that we got when doing the test internally. Interestingly, the test results that were misplaced were very similar between all 5 lay men. Importantly 80% of the misplaced test results were very close to the cut of value of 5 million progressive motile sperm cells per ml. The sensitivity of the SpermCheck test strip is rather poor i.e. the test cannot correctly identify men with normal semen quality and the NPV is extremely low i.e. the test is not able to tell the user with a negative test result if the sperm count is in fact low.

The invention claimed is:

1. A method of separating motile cells from non-motile cells in a sample, the method comprising the steps of:
providing a structure with a sample application compartment, a conditioning medium compartment and an analysis chamber in connection with the conditioning medium compartment,
providing a cell permeable filter having a pore size in the range of 1 µm to 20 µm, allowing the motile cells to move through the cell permeable filter,
providing the sample application compartment below the cell permeable filter and providing the conditioning medium compartment above the cell permeable filter,
providing a sample inlet port for placing the sample in the sample application compartment by a channel in fluid communication into the sample application compartment, providing a pressure release function of the conditioning medium compartment by a medium inlet port in fluid communication with an ambient environment, providing a conditioning medium by one of the following steps: initially providing the conditioning medium in at least the conditioning medium compartment of the sample chamber, adding the conditioning medium to the conditioning medium compartment through one of the analysis chamber or the medium inlet port, applying a sample containing motile cells below the cell permeable filter, through the sample inlet port being in fluid communication, via the channel, with the sample application compartment, the motile cells actively transporting themselves in any given direction in the liquid of the sample, the motile cells actively transporting themselves overcoming the gravitational force exerted on them, and the motile cells transporting themselves through the cell permeable filter by swimming by the cells themselves, and performing at least one of the following steps in the analysis chamber, subsequent to the motile cells having transported themselves through the cell permeable filter and into the analysis chamber: analysing, quantifying, extracting motile cells in the analysis chamber.

2. A method of extracting motile mammalian sperm cells from a sample containing motile cells and non-motile cells, the method comprising the steps of:

providing a structure with a sample application compartment, a conditioning medium compartment and an analysis chamber in connection with the conditioning medium compartment, providing a sample chamber providing a cell permeable filter having a pore size in the range from 1 μm to 20 μm, placing the cell permeable filter in the sample chamber so that a sample application compartment having a sample application compartment volume is defined below the cell permeable filter, and a conditioning medium compartment having a conditioning medium compartment volume is defined, wherein the sample application compartment volume is larger than the conditioning medium compartment volume, providing a sample inlet port for placing the sample in the sample application compartment by a channel in fluid communication into the sample application compartment, providing a pressure release function of the conditioning medium compartment by a medium inlet port in fluid communication with an ambient of the structure, providing a conditioning medium by one of the following steps: initially providing the conditioning medium in at least the conditioning medium compartment of the sample chamber, adding the conditioning medium to the conditioning medium compartment through one of the analysis chamber or the medium inlet port, applying a sample containing motile mammalian sperm cells in the sample application compartment, through the sample inlet port being in fluid communication, via the channel, with the sample application compartment, allowing motile mammalian sperm cells in the sample to move from the sample application compartment, through the cell permeable filter to the conditioning medium compartment by means of the motile cells actively transporting themselves overcoming the gravitational force exerted on them the motile cells transporting themselves through the cell permeable filter by swimming by the cells themselves, and extracting motile mammalian sperm cells having moved through the cell permeable filter.

* * * * *